(12) United States Patent
Hiltner

(10) Patent No.: US 10,602,984 B2
(45) Date of Patent: Mar. 31, 2020

(54) MEDICANT-RELEASING INTRAVASCULAR COMPONENTS AND METHODS

(71) Applicant: ACIST MEDICAL SYSTEMS, INC., Eden Prairie, MN (US)

(72) Inventor: Jason F. Hiltner, Minnetonka, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 781 days.

(21) Appl. No.: 15/093,203

(22) Filed: Apr. 7, 2016

(65) Prior Publication Data

US 2017/0215803 A1 Aug. 3, 2017

Related U.S. Application Data

(60) Provisional application No. 62/288,512, filed on Jan. 29, 2016.

(51) Int. Cl.
*A61B 5/00* (2006.01)
*A61B 5/0215* (2006.01)
(Continued)

(52) U.S. Cl.
CPC .......... *A61B 5/6876* (2013.01); *A61B 5/0022* (2013.01); *A61B 5/026* (2013.01); *A61B 5/02158* (2013.01); *A61B 5/68* (2013.01); *A61B 5/7278* (2013.01); *A61M 5/168* (2013.01); *A61M 25/0662* (2013.01);
(Continued)

(58) Field of Classification Search
None
See application file for complete search history.

(56) References Cited

U.S. PATENT DOCUMENTS 6,622,367 B1 * 9/2003 Bolduc .................. A61B 17/22
29/447
8,298,156 B2 10/2012 Manstrom et al.
(Continued)

OTHER PUBLICATIONS

Bulluck et al., "Reducing myocardial infarct size: challenges and future opportunities," Heart, vol. 102, No. 5, Mar. 1, 2016, pp. 341-348.
(Continued)

*Primary Examiner* — Michael R Bloch
(74) *Attorney, Agent, or Firm* — Fredrikson & Byron, P.A.

(57) ABSTRACT

Methods, systems, and devices are disclosed for administering one or more medications useful for facilitating diagnostic and/or surgical procedures within a patient. A guidewire is positioned intravascularly in a patient at a location of interest, the guidewire being free of any coating that includes adenosine. An intravascular component having a surface with a coating that includes a vasodilation agent is deployed over the guidewire. The vasodilation agent is released from the surface of the intravascular component, such as by eluting the vasodilation agent from the coating of the surface while the intravascular component is within the anatomical structure of the patient. The intravascular component is removed over the guidewire, and the guidewire is left at the location of interest after the intravascular component is removed, which can facilitate subsequent deployment of a different intravascular component over the guidewire.

18 Claims, 4 Drawing Sheets

(51) Int. Cl.
　　　*A61B 5/026* (2006.01)
　　　*A61M 5/168* (2006.01)
　　　*A61M 25/06* (2006.01)
　　　*A61M 25/09* (2006.01)
　　　*A61B 5/02* (2006.01)
　　　*A61M 25/00* (2006.01)
(52) U.S. Cl.
　　　CPC .............. *A61M 25/09* (2013.01); *A61B 5/02* (2013.01); *A61M 2025/0057* (2013.01); *A61M 2025/09133* (2013.01)

(56) References Cited

U.S. PATENT DOCUMENTS

| | | | |
|---|---|---|---|
| 8,771,310 B2 | 7/2014 | Forman et al. | |
| 2003/0093027 A1* | 5/2003 | McGuckin, Jr. | A61M 1/285 604/6.16 |
| 2010/0036411 A1* | 2/2010 | Forman | A61L 31/10 606/194 |
| 2010/0331813 A1* | 12/2010 | Robinson | A61B 5/0215 604/503 |
| 2013/0216481 A1* | 8/2013 | Rosenmeier | A61K 49/0004 424/9.1 |
| 2013/0303914 A1* | 11/2013 | Hiltner | A61B 8/12 600/449 |
| 2015/0196210 A1* | 7/2015 | McCaffrey | A61B 5/02158 600/488 |

OTHER PUBLICATIONS

Ko et al., "Hepatic arterial infusion pump chemotherapy for colorectal liver metastases: an old technology in a new era," Current Oncology, vol. 21, No. 1, Feb. 2014, pp. e116-e121.

Lim et al., "Slow infusion of calcium channel blockers compared with intravenous adenosine in the emergency treatment of supraventricular tachycardia," Resuscitation, vol. 80, No, 5, May 2009, pp. 523-528.

Wu et al., "Regional Arterial Infusion Chemotherapy improves the Pathological Response rate for advanced gastric cancer with Short-term Neoadjuvant Chemotherapy," Scientific Reports, vol. 5, No. 17516, Dec. 1, 2015, pp. 1-10.

* cited by examiner

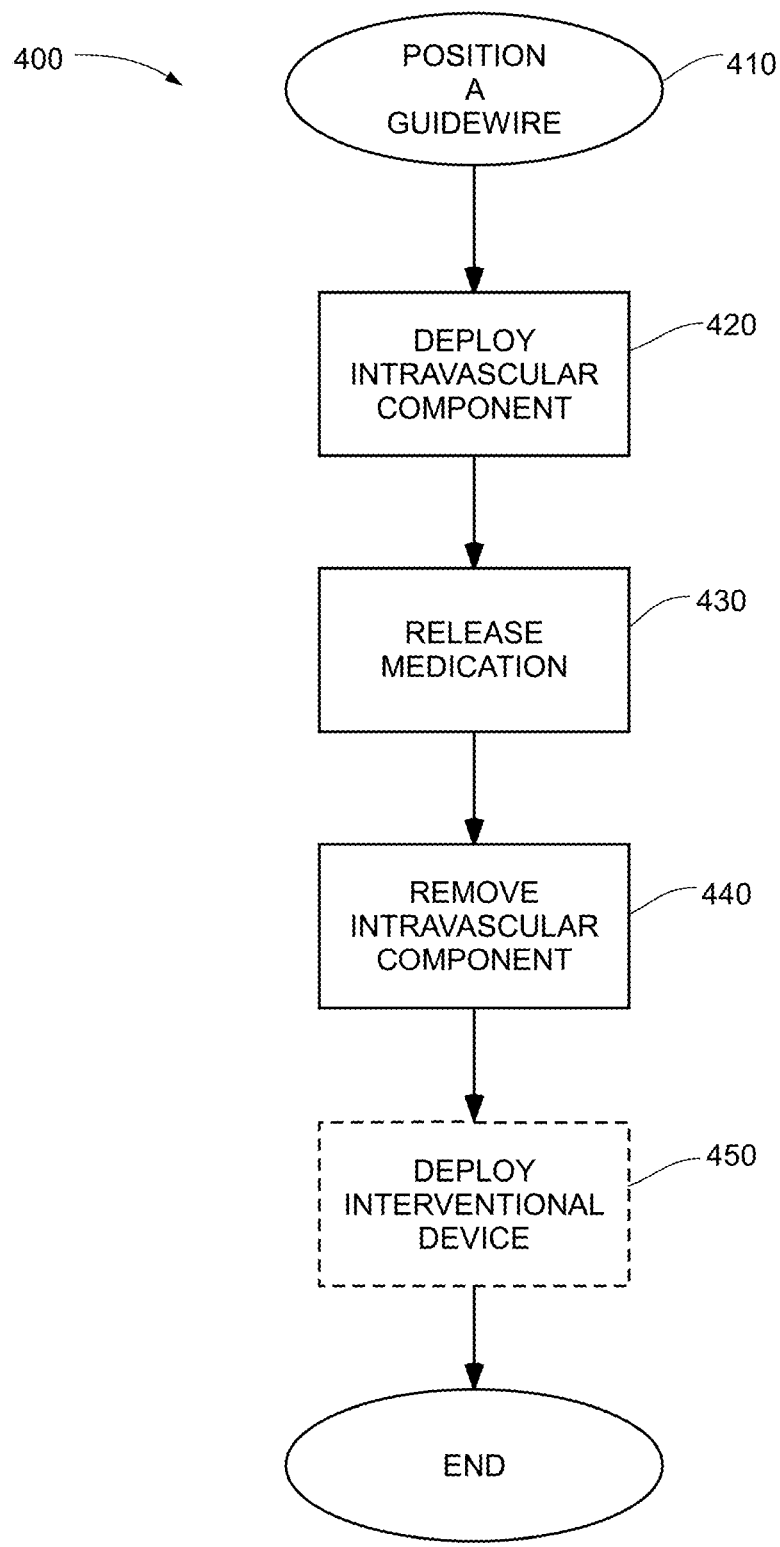

MEDICANT-RELEASING INTRAVASCULAR COMPONENTS AND METHODS

TECHNICAL FIELD

This disclosure relates generally to medical device technology and, more particularly, to devices and methods for releasing a medication from an intravascular component.

BACKGROUND

Many medical diagnostic and surgical procedures involving a patient include administration of a medication within the patient in conjunction with such procedures. In certain medical diagnostic and/or surgical procedures, the medication is typically administered to the patient in one of two ways. The first is via systematic intravenous (IV) injection of the medication using an IV bag and pump. The second is via intravascular delivery of a bolus of the medication through a port defined in a catheter inserted generally within an anatomical structure of a patient.

However, these typical medication administration techniques used in conjunction with certain medical diagnostic and/or surgical procedures have disadvantages. As for IV administration, additional equipment, such as a pump, IV bag, etc., is usually required in addition to that needed for the diagnostic and/or surgical procedure. Furthermore, IV administration usually will necessitate acquisition of a separate access point on the patient, in addition to any access point needed for the diagnostic and/or surgical procedure. The use of a separate access point for IV administration can result in longer administration duration, relative to intravascular administration, given the generally greater distance that the medication needs to pass from the separate access point to the procedure's region of interest. This longer administration duration can cause varying levels of discomfort for patients.

As for intravascular administration, although the administration duration can be shorter, and thus result in less discomfort for the patient, accurate placement of the catheter port is key. In other words, accurate placement of the catheter itself generally may not be sufficient since the port is the administration point. In addition, given that the catheter must be at or near the region of interest to correctly administer the medication, the presence of the catheter in this region can interfere with the relevant procedure (e.g., the use of other devices). This can especially be the case where the medication requires precise administration to the region of interest (e.g., the medication has a short half-life, the medication must not flow to other regions, etc.) and/or where the procedure requires precise measurements which can be obstructed by the catheter's presence.

SUMMARY

This disclosure in general describes various intravascular components, and related methods, which can be utilized to administer one or more medications for facilitating diagnostic and/or surgical procedures within a patient. In general, various embodiments can be utilized so as to start release of one or more medication(s) from a coating on a surface of an intravascular component when the component is deployed within an anatomical structure of a patient and stop release of the one or more medication(s) from the coating when the component is removed from the anatomical structure. Yet, these embodiments can still allow for other parts necessary for subsequent procedures to remain within the anatomical structure of the patient without releasing medication within the anatomical structure. Thus, various embodiments can allow for medication to be released during a time when such medication is useful for facilitating a certain procedure, and stop release of the medication when it is not needed for a subsequent, potentially related, procedure.

One embodiment includes a method where a guidewire is positioned intravascularly in a patient at a location of interest, where the guidewire is free of any coating comprising a vasodilation agent. For example, the guidewire can be free of any coating comprising adenosine. An intravascular component having a surface including a coating comprising one or more medicaments (e.g., including a vasodilation agent) is deployed over the guidewire, and may, for instance, be advanced over the guidewire so as to be at or near the location of interest. The medicament (e.g., including the vasodilation agent) is released from the surface of the intravascular component, such as by eluting the medicament from the coating of the surface while the intravascular component is within the anatomical structure of the patient (e.g., at or near the location of interest). The intravascular component is removed over the guidewire, and the guidewire is left at the location of interest after the intravascular component is removed. This may facilitate a subsequent interventional procedure over the guidewire, such as deployment of a second intravascular component over the guidewire.

Other embodiments can include an intravascular sensor delivery device as well as a system incorporating such intravascular sensor delivery device.

Embodiments of devices and methods disclosed herein may be used, for example, in diagnostic applications, such as cardiovascular procedures in coronary arteries, interventional radiology applications in peripheral arteries, and structural heart applications in heart valves.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings.

FIG. 4 is a flow diagram illustrating a method for performing an intravascular procedure.

DETAILED DESCRIPTION

The following detailed description is exemplary in nature and is not intended to limit the scope, applicability, or configuration of the invention in any way. Rather, the following description provides some practical illustrations for implementing examples of the present invention. Those skilled in the art will recognize that many of the noted examples have a variety of suitable alternatives.

Figure 1:
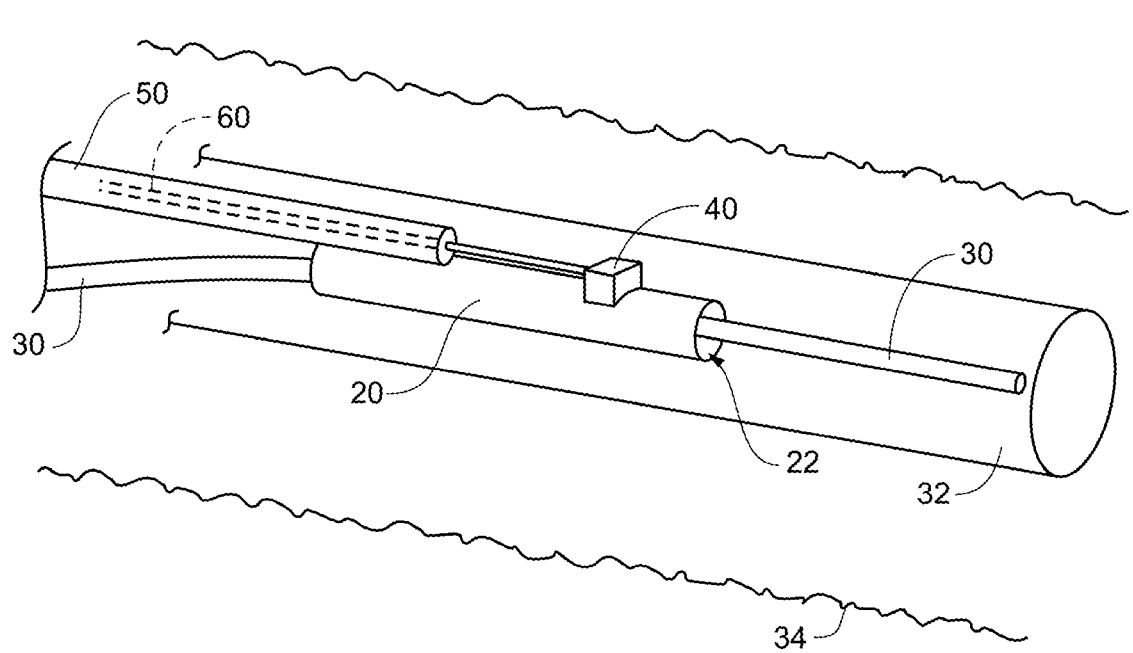
FIG. 1 is a perspective view of an embodiment of an intravascular component deployed over a guidewire positioned within an anatomical structure of a patient.

FIG. 1 illustrates a perspective view of one example of an intravascular component 10. The exemplary intravascular component 10 shown in FIG. 1 is an intravascular sensor delivery device. However, other embodiments of an intravascular component can include various other vascular measurement devices as well as devices that be used in vascular interventional procedures.

The intravascular sensor delivery device 10 of FIG. 1 includes a distal sleeve 20 having a guidewire lumen 22 for slidably receiving a guidewire 30 (e.g., a medical guidewire). The guidewire 30 can be positioned at (e.g., across) a location of interest within an anatomical structure of a patient prior to being received within the guidewire lumen 22. Coupled to the distal sleeve 20 is a sensor 40. The sensor 40 can be capable of sensing and/or measuring a physiological parameter of a patient and generating a signal representative of the physiological parameter. Thus, the distal sleeve 20, and hence the sensor 40, may be positioned within an anatomical structure of a patient (e.g., within a vein, artery, or other blood vessel, or across a heart valve, for example) by deploying the device 10 over the guidewire 30 to a location of interest. For instance, the distal sleeve 20 can slide over the positioned guidewire 30 to a desired point at the location of interest within the anatomical structure of the patient.

The device 10 as shown also includes a proximal portion 50, which is coupled to the distal sleeve 20. The proximal portion 50 includes a communication channel 60 for communicating the signal from the sensor 40 to a location outside of the patient (e.g., to a processor, display, computer, monitor, another medical device, etc.). In one example, the communication channel 60 may include a fiber optic communication channel, such as where the sensor 40 is a fiber optic pressure sensor. In some embodiments, the communication channel 60 can include an electrically conductive medium, such as one or more electrical conducting wires. Of course, many other forms of communication media may be suitable for transmitting the signal generated by sensor 40 to a location outside of the patient. In some embodiments, the communication channel 60 may include any of a variety of fluid and/or non-fluid communication media, such as a wireless communication link, or an infrared capability, or acoustic communications such as ultrasound, as examples.

The proximal portion 50 is also adapted, in the illustrated embodiment, to assist an operator (e.g., a physician or other medical personnel) in positioning the distal sleeve 20 and the sensor 40 within an anatomical (e.g., vascular) structure of the patient. This is typically accomplished by an operator first inserting guidewire 30 into a patient's vasculature and advancing it past the location of interest. The device 10 is then deployed by "threading" the distal sleeve 20 onto the guidewire 30, such that the lumen 22 slides over the guidewire 30, and advancing the distal sleeve 20 (and the associated sensor 40) by moving (e.g., pushing and/or pulling) the proximal portion 50 until sensor 40 is at the location of interest.

In certain embodiments, the guidewire lumen 22 may be sized to slide over "standard" sized medical guidewires. For example, a number of manufacturers make medical guidewires that range in size from less than about 0.014 inches outer diameter to more than about 0.038 inches outer diameter, typically having a finite number of common sizes within this range. "Standard" size medical guidewires might, for example, have outer diameters of 0.010, 0.014, 0.018, 0.021, 0.025, 0.028, 0.032, 0.035, and 0.038 inches. Thus, embodiments can include the guidewire lumen 22 sized appropriately to slide over a particular standard size medical guidewire. A device according to various embodiments may therefore be made available in a range of sizes corresponding to standard medical guidewire sizes.

One potential advantage of embodiments of the device 10 is that it can allow medical personnel to use the guidewire of their choice, since the device 10 can be sized so as to be used with any guidewire. Medical personnel may, for example, choose a particular guidewire based on its unique flexing and torque characteristics for certain procedures. Device 10 according to various embodiments thus provides medical personnel with the ability to use whichever guidewire is deemed best suited for a particular application.

Another potential advantage of the device 10 is that it does not require repositioning of the guidewire in order to make sensor readings. Once the guidewire has been positioned across the location of interest (e.g., a stenotic lesion), the device 10 can be positioned (e.g., advanced and/or retracted) over the guidewire and the sensor 40 can therefore be advanced and/or retracted across locations (e.g., lesions) to take measurements (e.g., pressure readings), for example, without moving the guidewire. Medical personnel may also save time by not having to reposition the guidewire across the locations to make such measurements, which also may cause discomfort to the patient.

Furthermore, in various embodiments such as that illustrated in FIG. 1, other advantages can result due to the configuration of the device 10 and guidewire 30 as separate components. In some examples, the distal sleeve 20 of the device 10 may be substantially concentric with the guidewire 30. The coupling of the proximal portion 50 to the distal sleeve 20 allows the guidewire 30 to separate from the rest of device 10 (e.g., in what is sometimes referred to as a "monorail" catheter configuration). The guidewire 30 and device 10 in such examples would both exit the patient as separate devices. Having the device 10 and guidewire 30 separate allows medical personnel to independently control device 10 and guidewire 30, as needed. This may also allow medical personnel to use a shorter guidewire. For example, a monorail-type configuration may allow for the use of a guidewire that is approximately 170 to 200 cm long, whereas an "over-the-wire" configuration might require the use of a much longer (e.g., up to 300 cm or more) guidewire. Having the device 10 and guidewire 30 as separate components (except at the distal sleeve 20) may also result in less friction (e.g., within the guide catheter 32) than if the device 10 and guidewire 30 had to be moved together in all instances as a unit.

As also shown in the example of FIG. 1, the device 10 can be deployed, at least in part, using a guide catheter 32. The guide catheter 32 can be placed within an anatomical structure of the patient, which in this example is blood vessel 34 which could, for example, be a coronary artery of the patient. The device 10 and guidewire 30 can be manipulated inside the guide catheter 32 within the anatomical structure, here blood vessel 34, of the patient. In certain embodiments, the size or "footprint" (e.g., the width and/or the cross-sectional area) of device 10 may allow it to fit within certain standard sized guide catheters. For example, in particular diagnostic applications, it would be desirable to have device 10 deployed within a certain sized guide catheter (e.g., smaller than about 4 or 5 French (FR)).

Certain physiological measurements may be made by positioning a sensor within a patient, such as by using an intravascular component, for instance, in the form of the intravascular sensor delivery device 10 having the sensor 40 of FIG. 1. Such physiological measurements may include, for example, measurements of blood parameters, such as blood pressure, oxygen saturation levels, blood pH, etc. Some such measurements may have diagnostic value and/or may form the basis for therapy decisions. In some examples where the sensor 40 is to be used to measure a blood pressure within a vessel of a patient, the sensor 40 can be positioned within the guide catheter 32, such as shown in FIG. 1. In one such particular example, a blood pressure measurement upstream of a location of interest within the vessel (e.g., a lesion) can be made while the sensor 40 is positioned within the guide catheter 32. This may be useful since the pressure within the guide catheter 32 can be substantially constant and equal to a blood pressure at an end of the guide catheter 32.

One diagnostic application in which intravascular sensor delivery device embodiments may be well-suited is the measurement of Fractional Flow Reserve (FFR). The FFR measurement quantifies the degree to which a stenotic lesion, for example, obstructs flow through a blood vessel. To calculate the FFR for a given stenosis, two blood pressure measurements are taken. One pressure reading is taken on the distal side of the stenosis (downstream from the stenosis) and the other pressure reading is taken on the proximal side of the stenosis (upstream from the stenosis, towards the aorta). The FFR measurement compares the first and second pressure readings, such as a ratio of the distal pressure to the proximal pressure (e.g., maximal blood flow in a stenotic artery, taken distal to the lesion, to normal maximal flow). The pressure gradient, or pressure drop, across a stenotic lesion is an indicator of the severity of the stenosis, and thus the FFR measurement is a tool in assessing the severity of the stenosis. The more restrictive the stenosis is, the greater the pressure drop, and the lower the resulting FFR measurement.

The FFR measurement may be a valuable diagnostic tool. For example, the FFR measurement can be used as a criterion on which to base certain therapy decisions. Medical personnel may decide, for instance, to perform an interventional procedure (e.g., angioplasty or stent placement) when the FFR measurement for a particular stenotic lesion is below a predetermined threshold FFR measurement for that stenotic lesion. On the other hand, the physician may decide to forego such interventional procedure when the FFR measurement for the stenotic lesion is above the predetermined threshold FFR measurement. As such, the FFR measurement can serve as a decision point for guiding treatment decisions.

Figure 2:
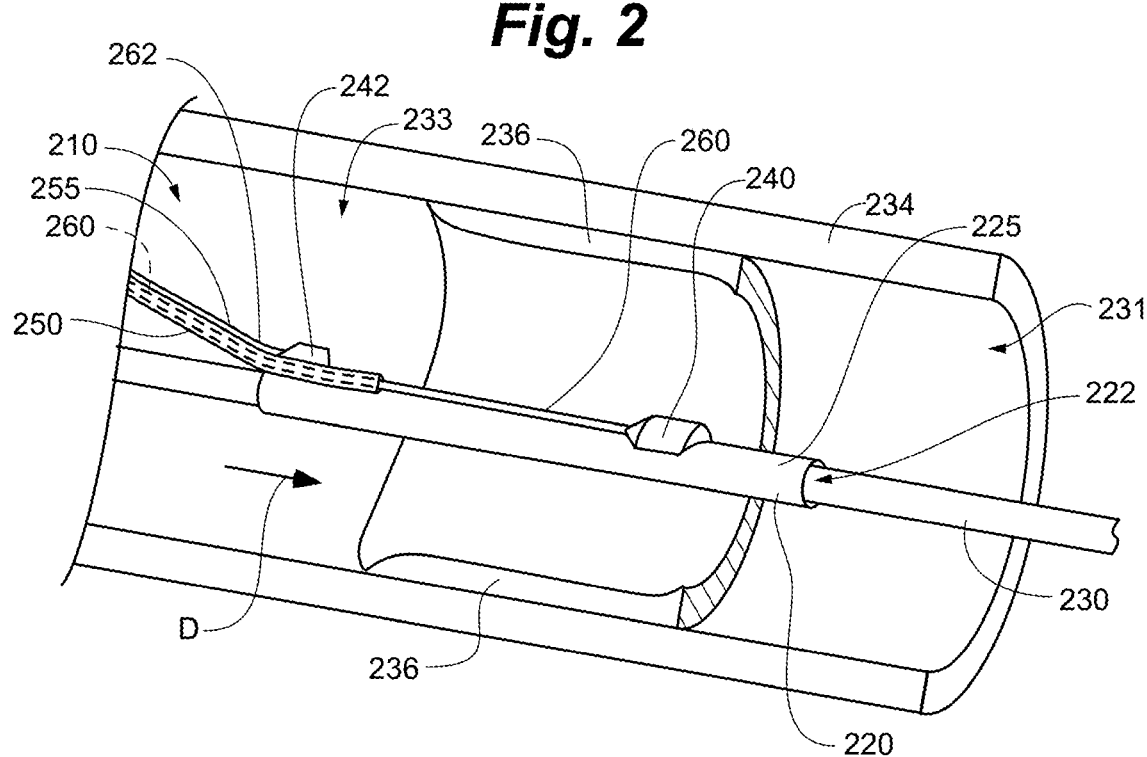
FIG. 2 is a perspective view of another embodiment of an intravascular component deployed over a guidewire positioned within an anatomical structure of a patient.

FIG. 2 illustrates a perspective view of another embodiment of an intravascular component, also shown as an intravascular sensor delivery device 210. The device 210 can be utilized to measure a variety of physiological parameters in a patient, although for illustrative purposes the example of FFR measurement in a blood vessel of a patient will be primarily referred to.

FIG. 2 shows the device 210 being deployed in a blood vessel 234 (e.g., a coronary artery) of a patient across a stenosis 236 (e.g., a stenotic lesion). To make an FFR measurement, for example, a first sensor 240 may be positioned to measure distal (downstream) blood pressure at a location 231 downstream of a location of interest, such as stenosis 236 in the example of FIG. 2. The first sensor 240 may then be repositioned to measure proximal (upstream) blood pressure at a location 233 upstream of location of interest stenosis 236. In one example, the blood pressure measurement upstream of the location of interest stenosis 236 can include a blood pressure measurement made while the sensor is positioned within a guide catheter (e.g., as shown in FIG. 1.) FFR may then be calculated approximately as the ratio of distal pressure to proximal pressure. The use of the terms "downstream" and "upstream" are with respect to the normal direction of blood flow, "D," as shown in FIG. 2.

In the example of FIG. 2, the first sensor 240 is coupled to a distal sleeve 220, such as to an outer surface 225 of the distal sleeve 220 as shown. The first sensor 240 is adapted to measure a physiological parameter of a patient, such as a blood parameter (e.g., blood pressure, temperature, pH, blood oxygen saturation levels, etc.), and generate a signal representative of the physiological parameter. In certain embodiments, the first sensor 240 is a fiber optic pressure sensor adapted to measure blood pressure. An example of a fiber optic pressure sensor is a Fabry-Perot fiber optic pressure sensor, which is a commercially available sensor. Examples of Fabry-Perot fiber optic sensors are the "OPP-M" MEMS-based fiber optic pressure sensor (400 micron size) manufactured by Opsens (Quebec, Canada), and the "FOP-MIV" sensor (515 micron size) manufactured by Fiso Technologies, Inc. (Quebec, Canada). In other embodiments, the first sensor 240 may be a piezo-resistive pressure sensor (e.g., a MEMS piezo-resistive pressure sensor), and in alternative embodiments the first sensor 240 may be a capacitive pressure sensor (e.g., a MEMS capacitive pressure sensor). A pressure sensing range from about −50 mm Hg to about +300 mm Hg (relative to atmospheric pressure), for example, may be desired for making most physiological measurements with the sensor 240.

Similar to that described for the device in FIG. 1, the device 210 shown in FIG. 2 can include the distal sleeve 220 shaped so as to slide, and thus be deployed, over a guidewire 230 within the anatomical structure of the patient. The distal sleeve 220 can have a guidewire lumen 222 sized for receiving the guidewire 230 as shown. For making an FFR measurement in a coronary artery 234, for example, the guidewire 230 may have an outer diameter of 0.014 inches, and guidewire lumen 222 would therefore need to have an inner diameter slightly larger than this to facilitate slidable movement of the distal sleeve 220 over the guidewire 230. The distal sleeve 220 can be formed of a flexible material in some embodiments to facilitate positioning and placement of the distal sleeve 220 (and sensor 240) over a guidewire 230 through narrow vascular structures, such as coronary arteries. In certain embodiments, the distal sleeve 220 comprises a flexible polyimide tube sized for placement in such narrow vascular structures. In further examples, the distal sleeve 220 may comprise a flexible microcoil tube. The length of the distal sleeve 220 may vary. In applications for coronary arteries, for example, the distal sleeve 220 may be up to about 15 inches long, including some embodiments having a length of 11 inches (e.g., to facilitate use deep within certain coronary arteries).

Also shown in FIG. 2 is a proximal portion 250 coupled to the distal sleeve 220. As shown here, a location on the outer surface 225 of the distal sleeve 220 is bonded to a location on an outer surface 255 of the proximal portion 250. Depending on the application of the device 210, it may be beneficial to bond the proximal portion 250 to the distal sleeve 220 at a location sufficiently proximal to the sensor 240 so that a bonding area between the proximal portion and the distal sleeve is not within the location of interest (e.g., not within a stenosis). The proximal portion 250 includes a communication channel 260 for communicating the physiological signal from the sensor 240 to a location outside of the patient (e.g., to a processor, display, computer, monitor, or to another medical device). The proximal portion 250 may be formed of a material of sufficient stiffness in order to assist an operator in positioning the distal sleeve 220 and the sensor 240 within an anatomical (e.g., vascular) structure of the patient. For example, in interventional cardiology procedures, at least a portion of the proximal portion 250 may be maneuvered within a guide catheter positioned within the aortic artery. The proximal portion 250 in such an application should therefore be flexible enough to accommodate the arch of the aorta, while being rigid enough to push and pull the device.

The communication channel 260 may be disposed along an outer surface of the proximal portion 250, or may be formed within the proximal portion 250, as shown in the example of FIG. 2. For example, communication channel 260 may comprise a communication lumen that extends longitudinally through proximal portion 250. Communication channel 260 may be similar to the communication channel described with respect to FIG. 1. In the embodiment shown in FIG. 2, communication channel 260 (e.g., a fiber optic cable) extends distally beyond proximal portion 250 and is coupled to sensor 240. The communication channel 260 in such an embodiment is at least partially housed within a communication lumen of the proximal portion 250.

FIG. 2 also shows an exemplary embodiment in which a second sensor 242 may be coupled to the device 210. For example, a second sensor 242 may be coupled to proximal portion 250 at the outer surface 255 such that the first and second sensors 240, 242 are spaced apart sufficiently (e.g., a fixed distance apart) to span a stenotic lesion. This embodiment may offer the ability to measure FFR without having to reposition the device 210. For instance, the first sensor 240 could be placed distal of the stenotic lesion 236 to measure distal pressure or other distal parameter, and second sensor 242 could be placed proximal of the stenotic lesion 236 to measure proximal pressure or other proximal parameter. The second sensor 242 may have a communication channel 262, which could be housed within proximal portion 250, or could be disposed along an outside surface of proximal portion 250, as shown in FIG. 2, for example. Thus, the first sensor 240 can measure a first blood pressure (or other parameter) distal (e.g., downstream) of the location of interest and generate a first signal representative thereof along channel 260, while the second sensor 242 can measure a second blood pressure (or other parameter) proximal (e.g., upstream) of the location of interest and generate a second signal representative thereof along channel 262. For instance, this could be done while the second sensor 242 is positioned within a guide catheter. In other embodiments the first and second sensors 240, 242 can utilize a common communication channel. The ability to measure proximal and distal parameters (e.g., pressures) substantially simultaneously may improve accuracy and/or reduce the effects of certain types of errors.

In various other examples, embodiments of an intravascular sensor delivery device can further include protective coverings, such as housings, for each of one or more sensors included as part of the device. A protective covering can serve to minimize or eliminate stresses that may be imparted on a sensor, such as when the device is traversing a vessel.

Figure 3:
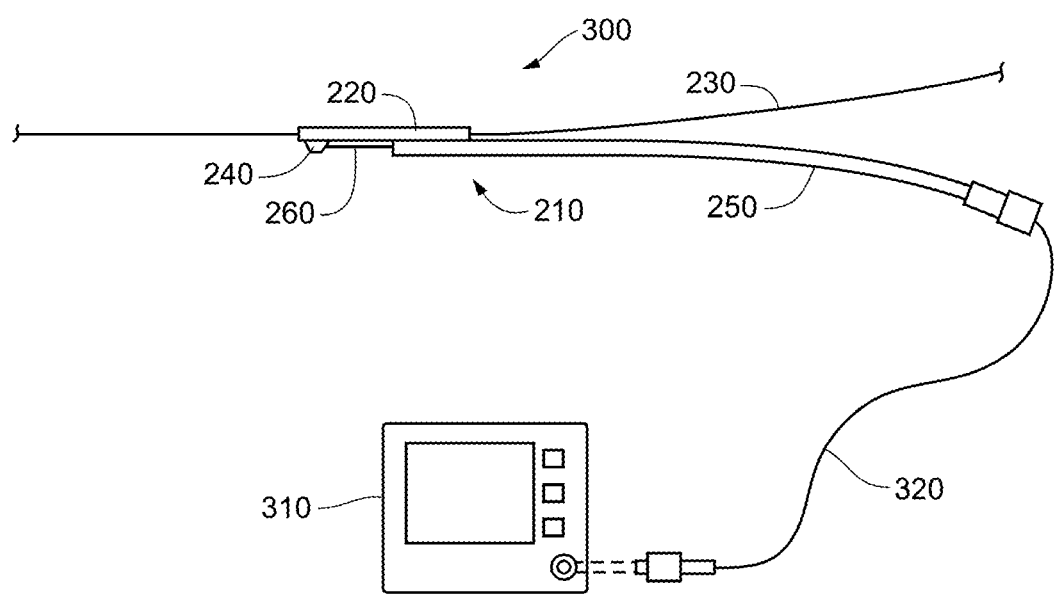
FIG. 3 is diagram showing an embodiment of a system where an intravascular component is in communication with a computing device.

FIG. 3 illustrates an exemplary system 300 where the device 210 (as described with respect to FIG. 2) is in communication with a computing device 310. Although the device 210 as described in FIG. 2 is shown here in communication with the computing device 310, any intravascular component can be used in the system 300. The system 300 can serve to allow the device 210, or other appropriate device, to interact with other devices and/or display and control equipment, such as via two-way communication.

The computing device 310 of the system 300 can be, for instance, a display and control unit having processing capabilities. As such, the computing device 310 may include a processor and one or more computer-readable storage mediums for storing instructions executable by the processor. The computing device 310 can be in communication with the device 210 via connection line 320. As shown, the connection line 320 can connect the computing device 310 with the device 210 at the proximal portion 250. As such, the connection line 320 can communicate with the sensor 240 via the communication channel of the proximal portion 250. Therefore, the computing device 310 can receive parameters (e.g., blood pressure measurements) or other data from the device 210 and act to process, via the processor, and display this data in a manner suitable for a specific application of the device 210. For example, where an FFR measurement is to be derived, the computing device 310 can communicate with the device 210 to receive proximal (e.g., upstream) and distal (e.g., downstream) blood pressure measurements and process this data to output the FFR measurement on a display of the computing device 310.

To facilitate many medical diagnostic and/or surgical procedures, one or more medications may need to be administered within the patient in conjunction with such procedures (e.g., before, during, and/or after a procedure). The following provides exemplary embodiments of intravascular components, and related methods, which can be utilized to administer one or more medications, such as for facilitating diagnostic and/or surgical procedures.

Depending on the application, such as the particular medical diagnostic and/or surgical procedure being performed, the one or more medicaments administered within the patient in conjunction with the specific application can vary. For instance, the following provides an exemplary, non-exhaustive listing of various medicaments that may be desirable to administer within the patient: carperitide; ciclosporin A; exenatide; metoprolol; heparin; regadenoson (lexiscan); papaverine; verapamil; diltiazem; floxuridine; nitroglycerin; nitroprusside; epirubicin; and oxaliplatin.

One or more of these medicaments can be included in a coating present on a surface of an intravascular component as appropriate for the specific application. As one example, in applications where a surgical procedure is to be performed to reduce a myocardial infarct size, a coating on a surface of an intravascular component can include carperitide, ciclosporin A, exenatide, and/or metoprolol. As a second example, where a surgical and/or diagnostic procedure is to be performed and coagulation is to be prevented during such procedure, a coating on a surface of an intravascular component can include heparin. As a further example, where a procedure is to be performed to treat supraventricular tachycardia, a coating on a surface of an intravascular component can include verapamil and/or diltiazem. As an additional example, where a procedure is to be performed to infuse chemotherapy, a coating on a surface of an intravascular component can include floxuridine, such as for hepatic artery infusion of chemotherapy, or one or both of epirubicin and oxaliplatin, such as for aterial infusion of chemotherapy.

As another example, in applications where a diagnostic procedure is to be performed in which an FFR measurement is to be obtained, accuracy of the FFR measurement can be significantly improved by administering a medication in conjunction with the diagnostic procedure. In particular, administering a mediation to induce hyperemia at the relevant area within the patient for the procedure can significantly improve the accuracy of the FFR measurement, and thus the particular diagnostic procedure. Therefore, embodiments can include an intravascular component having a surface including a coating containing one or more medications suitable for inducing hyperemia (e.g., regadenoson (lexiscan), papaverine, adenosine, nitroglycerin, and/or nitroprusside). In various embodiments, the surface of the intravascular component can include a coating comprising one or more vasodilation agents. As one example, the surface of the intravascular component can include a coating comprising adenosine. The one or more vasodilation agents (e.g., adenosine) may, in some examples, be eluted from the coating within a patient's body at the region being assessed in the procedure to cause vasodilation of a vessel at the region of interest through activation of one or more receptors (e.g., $A_1$ receptor).

For instance, in some examples a coating comprising adenosine and/or other vasodilation agent(s) can be included on at least a portion of a surface of the intravascular component embodied in such examples as an intravascular sensor delivery device (e.g., device 10 of FIG. 1, device 210 of FIG. 2). The coating comprising adenosine can be, for example, on at least a portion of an outermost surface of the intravascular sensor delivery device. The coating may thus form, in the example, a top layer of the intravascular sensor delivery device. More particularly, the coating can be included on at least a portion of the outer surface of the distal sleeve (e.g., the outer surface 225 of the distal sleeve 220 in FIG. 2) in one embodiment. In another example, the coating can be included on at least a portion of the outer surface of a guide catheter (e.g., guide catheter 32 in FIG. 1), if used. In some cases, it may be useful to include the coating comprising adenosine around the outer surface perimeter over at least a portion of the length of the outer surface (e.g., 360 degrees of a cross-section taken perpendicular to a longitudinal axis of a component, such as a circumference where the component, and thus outer surface, is generally cylindrical). Before applying the coating, where the outer layer of the distal sleeve is a polyester (PET) covering, the PET covering can be plasma treated and the coating comprising adenosine then applied so as to form the outer layer of the distal sleeve at the location(s) where the plasma treatment occurred. In one example, the outer surface can include adjacent portions of PET and the coating comprising adenosine. In another example, where the entirety of the outer surface of the distal sleeve is plasma treated, the entirety of the outer surface of the distal sleeve can include the coating comprising adenosine. In other examples, the coating comprising adenosine can be directly applied to the outer surface of the distal sleeve (e.g., such that the coating is on top of the PET covering, at least at one portion).

Including the coating comprising one or more medications (e.g., vasodilation agent) on at least a portion of an intravascular component surface can allow the medication to be directly released from the surface of the component while the component is within an anatomical structure of a patient. In some embodiments, the composition of the coating can be structured so that the medication is released when the intravascular component, and thus coating thereon, comes into contact with bodily fluid within the anatomical structure of the patient. For example, the coating comprising adenosine included on the surface of the intravascular component can have properties designed to cause the coating to release (e.g., elute) adenosine from the surface of the component due to a chemical reaction with fluid (e.g., blood) within the patient's body. This may include continuous release of adenosine from the coating on the surface of the component over a period of time during which the coating is in contact with the fluid, such as fluid within the location of interest.

In some embodiments, the coating may be structured so that the reaction between the coating and the fluid with the patient's body begins to occur only when the fluid contacting the coating is flowing at a velocity above or below a predetermined threshold velocity. In these embodiments, the coating can be structured so that once the coating is contacted by fluid flowing at or above the threshold velocity, the coating continuously releases the medication (e.g., elutes vasodilation agent(s), such as adenosine) over the time period in which the coating and fluid flowing at or above the threshold velocity are in contact. This may be useful in instances where it is desired to only release the medication from the coating at a particular, targeted area within a patient that may be defined by a particular distinguishing blood flow rate or range.

In one exemplary application, where the intravascular component is to ultimately be used in a procedure in a coronary artery, the component may first need to pass through other regions within the patient at which it is not desirable to release medication from the coating before arriving at the region of interest within the coronary artery where medication is desired to be released. Due to a coronary artery, for instance, having a blood flow rate that can generally differ from an initial entry point of the component on the patient, the coating on the surface of the component can be structured so as to release the medication at the region of interest within the coronary artery but not at the initial entry point and/or other various locations therebetween having blood flow rates below the predetermined threshold velocity. In one example the coating can be structured so that medication (e.g., vasodilation agent(s), such as adenosine) is eluted from the coating on the surface of the component continuously while the coating is in contact with blood flowing at a velocity of 20 cm per second or greater. In another example, the coating can be structured so that medication (e.g., vasodilation agent(s), such as adenosine) is eluted from the coating on the surface of the component continuously while the coating is in contact with blood flowing at a velocity of 10 cm per second or greater. This can also be useful when the component is to be removed from the region of interest within the coronary artery, and thus comes into contact with blood flow rates below the predetermined threshold velocity (e.g., 20 cm/s, 10 cm/s) at other regions. This similarly can prevent medication from being released at undesirable regions within the patient during removal of the component, at least in instances where the coating on the surface of the component has medication remaining.

Additionally, or alternatively, the coating on the surface of the component can be structured so as to release the medication after having been in contact with bodily fluid within an anatomical structure of a patient for a predetermined period of time. One example can include a procedure where the intravascular component is to be used in a coronary artery but will first pass through one or more other regions, where it may not be desirable to release medication from the coating. Here, the intravascular component can include the coating on the surface of the component structured such that a chemical reaction between the coating and the bodily fluid requires a period of time, substantially equal to the time it normally takes to advance the component to the coronary artery, to result in elution of the medication. In one example, the coating on the surface of the component can be structured such that a chemical reaction between the coating and the bodily fluid (e.g., blood) requires about 20 or more seconds before medication is released into the patient from the coating. Thus, the initial contact between the bodily fluid and the coating may not cause the medication to elute from the coating, but rather contact between the bodily fluid and the coating may need to be present for a particular period of time to allow a chemical reaction to occur and result in release of the medication from the coating. In other embodiments, the coating can be structured so that a chemical reaction between the coating and the bodily fluid (e.g., blood) causes medication from the coating to be released into the patient substantially at the same time the coating comes into contact with the bodily fluid.

In addition to the coating having properties designed to cause release of the medication(s) due to contact with bodily fluid (e.g., velocity, time, etc.), the coating can also be structured to deliver appropriate dosage of the medication. For instance, in the example where a diagnostic procedure includes obtaining an FFR measurement and administering adenosine as the medication to induce hyperemia, the coating comprising adenosine can be structured to release (e.g., elute) at an appropriate dose rate. This can include a coating structured to elute adenosine upon contact with blood within a patient's vessel at a rate sufficient to fully induce hyperemia. This can further include a coating structured to elute adenosine upon contact with blood within a patient's vessel at a minimum required dosage. This can allow for automatic delivery of the medication at the correct dosage for the specific application when the intravascular component including the coating is within the vessel.

As one example, where the intravascular component is within a coronary vessel, the coating can be structured to release adenosine and/or other vasodilation agent(s) at a dose rate between approximately 40 and 60 micrograms per minute. In other examples where the component is within a coronary vessel, the coating can be structured to release adenosine and/or other vasodilation agent(s) at a dose rate between approximately 40 and 80 micrograms per minute or between approximately 40 and 100 micrograms per minute. The coating may also be structured to release adenosine continuously for a period of time of at least 40 minutes. In fact, relatively long periods of adenosine administration may act to reduce detrimental effects of micro-embolization in the vasculature that can result from intravascular interventional procedures. In some embodiments, the coating can be structured so as to release medication (e.g., elute adenosine) only when fluid in contact with the coating is above or below a predetermined threshold velocity, and when such fluid velocity is present to release medication continuously at the desired dose rate (e.g., 40-60 micrograms per minute). The coating can further be structured to meet dosage safety requirements for a particular diagnostic and/or surgical procedure. In one embodiment, the coating may be structured so as to not release more than 500 micrograms of adenosine within any ten second period of time under foreseeable use conditions in such procedure.

Releasing the medication to be used in conjunction with the particular diagnostic and/or surgical procedure directly from the intravascular component, such as the intravascular sensor delivery device, can provide advantages. For example, because the intravascular sensor delivery device being used in a procedure generally needs to be placed at the region of interest so as to measure relevant parameters (e.g., blood pressure), the medication may be administered only at the specific region of interest within a vessel. In FFR measurements in a coronary vessel, eluting adenosine and/or other vasodilation agent(s) directly from the intravascular sensor delivery device can vasodilate only the relevant mass of myocardium, and not areas outside that needed for the procedure, given that the intravascular sensor delivery device is placed in the vessel at the lesion under evaluation.

FIG. 4 shows a flow diagram illustrating a method 400 for performing an intravascular procedure, including administration of a medication as described above. At step 410, a guidewire, such as that shown and described with respect to FIGS. 1 and/or 2, is positioned intravascularly in a patient at a location of interest. For instance, the guidewire can be inserted within a vessel of a patient and positioned so as to encounter the location of interest (e.g., stenotic lesion), span across the location of interest, and traverse past the location of interest. In various embodiments, the guidewire used in step 410 has an outer surface of the guidewire that is free of a coating comprising a vasodilation agent (e.g., a guidewire that is free of a coating comprising adenosine). In one example, using a guidewire having a surface free of a coating comprising adenosine can be advantageous. In fact, a guidewire that does include a coating comprising adenosine may result in the inducement of hyperemia for a period of time longer than desired and/or to a region within the patient that is unintended. This may result in unintended consequences, such as prolonged discomfort to the patient or other detrimental health consequences.

At step 420, an intravascular component is deployed over the guidewire positioned as described for step 410. The intravascular component can be any of an array of devices useful in various medical diagnostic and/or surgical procedures, such as vascular measurement devices as well as devices used in vascular interventional procedures. In one embodiment, the intravascular component can be an intravascular sensor delivery device, such as the device 10 of FIG. 1 or device 210 of FIG. 2. In such embodiment, the guidewire can be received by the device 10 or 210 as described above so that the device is able to slide over the guidewire and advance to the location of interest within the vessel. In some cases, advancing the intravascular component to the location of interest can include advancing the component so as to be at the location of interest, which can include the component being positioned at a stenotic lesion as well as immediately upstream of and/or downstream of a stenotic lesion.

The intravascular component deployed over the guidewire in step 420 has a surface including a coating comprising adenosine and/or other medication useful in conjunction with the particular diagnostic and/or surgical procedure. The surface having the coating comprising adenosine and/or other medication can be similar to that described previously.

At step 430, the medication is released from the coating on the surface of the intravascular component. The medication (e.g., adenosine and/or other vasodilation agent(s)) can be released from the coating by eluting medication from the coating of the surface of the intravascular component while such component is deployed within a vessel of a patient. For instance, as described previously, the medication can be eluted by reacting the coating with fluid within the patient's vessel upon contact therebetween. Thus, deployment of the intravascular component having the coating may act to start release of the medication from the surface of the intravascular component. In some embodiments as described previously, the coating can have a structure such that certain blood flow velocities need be present to trigger the release of the medication from the coating. In addition to or alternatively, the coating can have a structure to release medication only after a predetermined duration of contact between the coating and blood as appropriate for the particular procedure. In addition to or alternatively, the coating can have a structure to release appropriate dosage of the medication for the particular procedure.

In some embodiments, once at least a portion of the medication has been released from the coating, various relevant procedural steps may be performed. In the example of an FFR measurement, after at least a portion of adenosine has been released from the surface of the intravascular component (e.g., intravascular sensor delivery device 10 or 210) a first blood pressure can be measured upstream of the location of interest (e.g., stenotic lesion) and a second blood pressure can be measured downstream of the location of interest. In embodiments where the component includes a single sensor, a first measurement can be taken and then the component may be repositioned relative to the location of interest to take a second measurement over a period of time while adenosine is released from the coating on the surface of the component. In embodiments where the component includes two sensors positioned upstream and downstream of the location of interest, the first and second blood pressure measurements can be made substantially simultaneously while adenosine is released from the coating on the surface of the component.

In various embodiments, releasing medication from a coating on a surface of an intravascular component at step 430 can be utilized in a therapeutic manner. Therapeutic use of the intravascular component can be accomplished either in conjunction with a diagnostic and/or surgical procedure (e.g., during a fractional flow reserve measurement) or as a sole use of the intravascular component. As one example, releasing (e.g., eluting) adenosine and/or other medication from the coating on the surface of the intravascular component may treat tissue at a desired region within a patient. For instance, the release of adenosine and/or other medication from the coating can be used to treat tissue in the heart, such as by treating ischemic tissue following a myocardial infarction. Various other beneficial uses of the release of medication from the coating of the intravascular component can be achieved. For example, as noted previously, relatively long periods of adenosine administration from the coating of the intravascular component may act to reduce detrimental effects of micro-embolization in the vasculature that can result from intravascular interventional procedures.

At step 440, the intravascular component can be removed from the location of interest over the guidewire. In one example, this can include simply removing the intravascular component from the particular location of interest and moving the intravascular component to a new, different location of interest within the patient over the guidewire. In other examples, step 440 can include removing the intravascular component completely from the patient. Once the intravascular component is removed from the location of interest, this can result in stopping the release of medication from the coating at the location of interest, for instance because the coating is no longer in contact with fluid within the patient and/or because the coating is no longer is contact with fluid having a flow velocity above the predetermined threshold velocity. Thus, just as deploying the intravascular component having the coating at step 420 may act to start the release of medication from the surface of the component, removing the component having the coating at step 440 may act to stop the release of the medication within the patient.

Although step 440 includes removing the intravascular component from the location of interest, step 440 can also include leaving the guidewire within the anatomical structure of the patient after the component has been removed. Thus, even though the guidewire may remain within the location of interest, the release of medication at the location of interest may still be stopped by removal of the intravascular component. Therefore, the guidewire can remain within the anatomical structure of interest to facilitate a procedure (e.g., an interventional procedure) subsequent to the particular diagnostic and/or surgical procedure without continuing to release medication within the patient (e.g., facilitating subsequent deployment of a different intravascular component over the guidewire). For instance, in the example of a diagnostic procedure obtaining an FFR measurement, the method 400 can allow hyperemia to be induced only at the location of interest where the FFR measurement is being made and only during the FFR assessment itself. In one application, by inducing hyperemia only at the location of interest where the FFR measurement is being made only the relevant mass of myocardium is vasodilated.

The method 400 may include an additional, optional step at 450 of deploying a different intravascular component over the guidewire remaining within the location of interest after the first intravascular component has been removed. The second intravascular component may be an interventional device. As such the interventional device may be deployed over the guidewire at a time when release of the medication at the location of interest has been terminated due to the removal of the intravascular component. In one example, the deployment of an interventional device (e.g., stent, angioplasty device) over the guidewire at step 450 may occur depending on the FFR measurement. For instance, if the FFR measurement is below a predetermined threshold FFR measurement for the stenotic lesion then step 450 may take place (e.g., stent placement, angioplasty). However, if the FFR measurement is above a predetermined threshold FFR measurement for the stenotic lesion then step 450 may not occur. Where other medical diagnostic and/or surgical procedures are performed, the determination as to whether step 450 will occur can be based on various other criteria.

Various examples have been described. These and other examples are within the scope of the following claims.

The invention claimed is:
1. A method comprising the steps of:
positioning a guidewire intravascularly in a patient at a location of interest, the guidewire having an outer guidewire surface free of a coating that includes adenosine;
deploying, over the guidewire, a first intravascular component having a surface with a coating that includes a medicament, wherein deploying the first intravascular component over the guidewire includes advancing the first intravascular component over the guidewire to the location of interest;
eluting the medicament from the coating of the surface of the first intravascular component while the first intravascular component is at the location of interest; and
removing, over the guidewire, the first intravascular component and leaving the guidewire at the location of interest after removal of the first intravascular component to facilitate subsequent deployment of a second intravascular component over the guidewire, wherein removing the first intravascular component, and leaving the guidewire at the location of interest after removal of the first intravascular component, comprises stopping elution of the medicament at the location of interest.

2. The method of claim 1, further comprising the step of:
deploying, over the guidewire, the second intravascular component after the first intravascular component has been removed.

3. The method of claim 1, wherein the first intravascular component is an intravascular sensor delivery device.

4. The method of claim 3, further comprising the step of:
measuring, with a sensor coupled to the intravascular sensor delivery device, a first blood pressure upstream of the location of interest and a second blood pressure downstream of the location of interest, wherein both the first blood pressure and the second blood pressure are measured after at least a portion of the medicament has been eluted from the surface of the intravascular sensor delivery device.

5. The method of claim 4, wherein measuring the first blood pressure upstream of the location of interest comprises positioning the sensor within a guide catheter of the intravascular sensor delivery device.

6. The method of claim 4, wherein the sensor is a first sensor and further comprising a second sensor, the first blood pressure being measured by the first sensor within a guide catheter of the intravascular sensor delivery device so as to generate a first signal, and the second blood pressure being measured by the second sensor so as to generate a second signal, and wherein the first blood pressure and the second blood pressure are measured substantially simultaneously.

7. The method of claim 4, wherein the sensor comprises a single sensor, and the method further comprises the step of repositioning the intravascular sensor delivery device over the guidewire to be downstream of the location of interest, the repositioning being over a period of time while the medicament is released from the surface and after measuring the first blood pressure upstream of the location of interest.

8. The method of claim 4, further comprising the step of:
calculating, with a processor, Fractional Flow Reserve (FFR) as a comparison of the first blood pressure to the second blood pressure.

9. The method of claim 8, further comprising the step of:
deploying, over the guidewire, an interventional device after the first intravascular component has been removed when the calculated FFR is below a predetermined threshold FFR measurement.

10. The method of claim 8, wherein calculating FFR as the comparison of the first blood pressure to the second blood pressure comprises calculating FFR as a ratio of the second blood pressure to the first blood pressure.

11. The method of claim 8, wherein the location of interest within the patient comprises a stenotic lesion.

12. The method of claim 1, wherein eluting the medicament comprises eluting a vasodilation agent.

13. The method of claim 12, wherein eluting the vasodilation agent comprises eluting adenosine.

14. The method of claim 1, wherein eluting the medicament comprises eluting a medicament selected from the group consisting of: floxuridine, epirubicin, or oxaliplatin.

15. The method of claim 1, wherein eluting the medicament comprises eluting a medicament selected from the group consisting of: carperitide, ciclosporin A, exenatide, or metoprolol.

16. The method of claim 1, wherein the surface of the first intravascular component having the coating is an outermost surface of the first intravascular component.

17. The method of claim 16, wherein the first intravascular component is an intravascular sensor delivery device having a sensor coupled thereto, and the outermost surface of the first intravascular component is a distal sleeve of the intravascular sensor delivery device, and wherein deploying the first intravascular component over the guidewire comprises receiving the guidewire within a guidewire lumen of the distal sleeve of the intravascular sensor delivery device.

18. The method of claim 1, wherein eluting the medicament from the coating of the surface of the first intravascular component while the first intravascular component is at the location of interest comprises eluting a vasodilation agent from the coating, and wherein removing the first intravascular component and leaving the guidewire at the location of interest after removal of the first intravascular component comprises stopping the elution of the vasodilation agent from the coating.

* * * * *